United States Patent [19]

Bagli et al.

[11] Patent Number: 5,191,084
[45] Date of Patent: Mar. 2, 1993

[54] PHENYL PYRAZOLIDINONES AS BRONCHODILATORS AND ANTI-INFLAMMATORY AGENTS

[75] Inventors: Jehan F. Bagli, Princeton; Louis J. Lombardo, Belle Mead, both of N.J.

[73] Assignee: American Home Products Corporation, New York, N.Y.

[21] Appl. No.: 694,197

[22] Filed: May 1, 1991

[51] Int. Cl.$^5$ ............................................ C07D 401/12
[52] U.S. Cl. ................ 546/279; 548/369.7; 548/370.4; 548/371.1; 548/366.1
[58] Field of Search ........................................ 546/279

[56] References Cited

PUBLICATIONS

Pasbrig et al. CA 99:212267m.

Primary Examiner—Jane T. Fan
Attorney, Agent, or Firm—George Tarnowski

[57] ABSTRACT

There are disclosed compounds of the formula

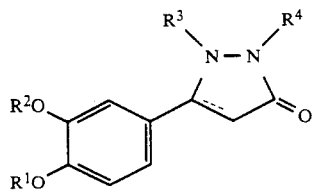

wherein
$R^1$ is hydrogen or lower alkyl;

$R^2$ is $C_{3-7}$ alkyl or $C_{3-7}$ cycloalkyl;
$R^3$ is hydrogen, lower alkyl, carboxyloweralkyl, lower alkoxycarbonyl, lower alkoxycarbonyl loweralkyl, aryl or aralkyl;
$R^4$ is hydrogen, $C_{1-8}$ alkyl,

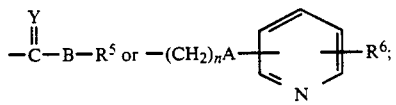

B is a bond, NH or O;
Y is O or S;
A is a bond or —C≡C—;
n is 0-5;
$R^5$ is hydrogen when B is NH, or
$R^5$ is lower alkyl, $C_{3-8}$ cycloalkyl; aryl, substituted aryl, aralkyl, substituted aralkyl, aralkenyl, aralkenylalkyl or

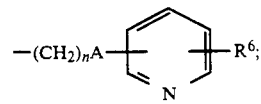

$R^6$ is hydrogen or halo;
the dotted line represents an optional double bond; and the pharmacologically acceptable salts thereof, which by virtue of their ability to selectively inhibit PDE IV, are bronchodilatory and anti-inflammatory and so are useful in the treatment of acute and chronic bronchial asthma and associated pathologies.

12 Claims, No Drawings

PHENYL PYRAZOLIDINONES AS BRONCHODILATORS AND ANTI-INFLAMMATORY AGENTS

This invention relates to novel phenyl pyrazolidinones having bronchodilator and antiinflammatory activity and being useful in the treatment of asthma.

Asthma is a disease in which respiratory distress is produced as a result of airway narrowing. This narrowing is caused largely by 1) the acute constriction of the respiratory smooth muscle that surrounds the airways and 2) chronic inflammation within the lung. Reversal of bronchospasm and prevention of pulmonary inflammation, then, are critical approaches to the relief of the symptoms of asthma.

One approach for reversing bronchospasm and also inhibiting inflammation is to elevate intracellular adenosine cyclic 3':5'-monophosphate (cAMP) in respiratory smooth muscle and inflammatory cells, respectively. The compound adenosine cyclic 3':5'-monophosphate is defined as a "second messenger" because it mediates a variety of effects performed by hormones, which are "first messengers". One of the more important roles is in mediating bronchodilation [see Sutherland et al., Circulation, 37, 279 (1968)]. The enzymatic mechanism for the inactivation of cyclic AMP has been known for some time [see Butcher et al., Pharmacologist, 1, 63 (1959)] and the enzyme responsible for this inactivation was identified as a magnesium dependent phosphodiesterase. The latter is capable of hydrolyzing cyclic AMP to adenosine monophosphate. Subsequent research has established that the xanthine-based bronchodilators, such as theophylline and aminophylline, mediate their bronchodilating activity via inhibition of cyclic AMP phosphodiesterase (PDE) [see Lancet 1970, 1119]. Agents that elevate smooth muscle cAMP concentrations induce rapid bronchodilation and inhibit the release of inflammatory mediators from activated leukocytes [see Hardman, in Smooth Muscle, An Assessment of Current Knowledge, Univ. of Texas Press, (1981); and Nielson et al., American Review of Respiratory Disease, 137, 25 (1988)]. By virtue of their dual mechanisms of action, such compounds can function as highly effective anti-asthmatic drugs.

Cyclic AMP concentrations within the living cell are determined by both the rate of its synthesis by adenylate cyclase and the rate of its degradation by phosphodiesterases. Thus, either stimulating adenylate cyclase or inhibiting PDEs in pulmonary tissues can result in anti-asthmatic activities. The most effective anti-asthmatic drugs are those which demonstrate the ability to inhibit a specific PDE, often called PDE IV, that selectively metabolizes cAMP and that is insensitive to the modulatory effects of guanosine cyclic 3':5'-monophosphate (cGMP) and calcium. This PDE is found in both respiratory smooth muscle and inflammatory cells, and has been demonstrated to be a principle regulator of cAMP in these tissues [see Torphy and Cieslinski, Molecular Pharmacology, 37, 206 (1990), and Dent et al., British Journal of Pharmacology, 90, 163P (1990)]. Moreover, a variety of phosphodiesterase isozymes have been isolated from bronchial smooth muscles [see Silver et al., Eur. J. Pharmacol., 150, 85 (1988)] and their kinetics have been studied using a variety of inhibitors.

The compounds of this invention not only are selective inhibitors of PDE IV of pulmonary tissue, but also inhibit the influx of leukocytes into the bronchial tissue. This influx is the cause of the inflammation which characterizes chronic asthma, and can lead to pulmonary edema [see Nseuli et al., Ann. Allergy, 60, 379 (2988)]. Since the compounds of the invention inhibit leukocyte influx into the bronchoalveolar lavage, they can also be used to prevent the onset of the inflammation which is characteristic of chronic asthmatic conditions. Consequently, the compounds named in this invention are both bronchodilatory and antiinflammatory, and are effective in animal models of allergic and nonallergic asthma. However, because the compounds of the invention preferentially inhibit the PDE IV isozyme, they are more selective and safer anti-asthmatics than nonselective PDE inhibitors currently used for the treatment of asthma, such as theophylline.

The invention provides novel compounds of the formula

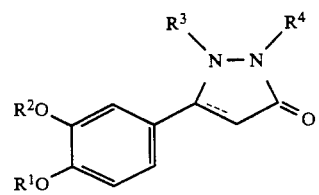

wherein
$R^1$ is hydrogen or lower alkyl;
$R^2$ is $C_{3-7}$ alkyl or $C_{3-7}$ cycloalkyl;
$R^3$ is hydrogen, lower alkyl, carboxyloweralkyl, lower alkoxycarbonyl, lower alkoxycarbonyl loweralkyl, aryl or aralkyl;
$R^4$ is hydrogen, $C_{1-8}$ alkyl,

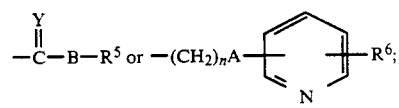

B is a bond, NH or O;
Y is O or S;
A is a bond or —C≡C—;
n is 0–5;
$R^5$ is hydrogen when B is NH, or
$R^5$ is lower alkyl, $C_{3-8}$ cycloalkyl, aryl, substituted aryl, aralkyl, substituted aralkyl, aralkenyl, aralkenylalkyl or

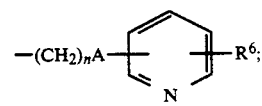

$R^6$ is hydrogen or halo;
the dotted line represents an optional double bond; and
the pharmacologically acceptable salts thereof.

The terms "lower alkyl" and "lower alkoxy" refer to moieties having 1 to 6 carbon atoms in the carbon chain. The term "aryl" refers to aromatic moieties having 6–10 carbon atoms, while "aralkyl" refers to moieties having 12–16 carbon atoms in the aromatic nucleus and associated alkyl chain. The term "aralkenyl" refers to moieties having 12–16 carbon atoms in the aromatic nucleus and associated alkylene chain, while "aralkenylalkyl" refers to "aralkenyl" moieties whose alkenyl chain is further attached to a lower alkyl chain. The term "halo" refers to fluoro, chloro and bromo.

The especially preferred compounds are those having the formula

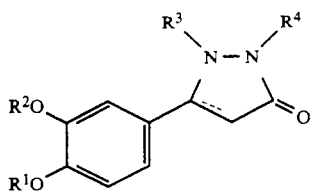

wherein
$R^1$ is $C_{1-3}$ alkyl;
$R^2$ is $C_{4-6}$ alkyl or $C_{5-6}$ cycloalkyl;
$R^3$ is $C_{1-3}$ alkyl or aralkyl;
$R^4$ is

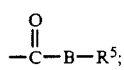

B is a bond or NH;
$R^5$ is hydrogen when B is NH; or aralkyl or

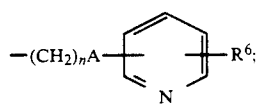

A is a bond or —C≡C—;
n is 0-2; and
$R^6$ is hydrogen or halo.

The most preferred compounds are those having the formula

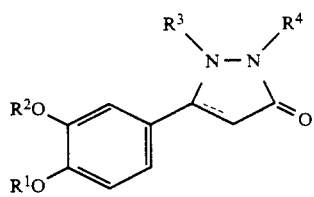

wherein
$R^1$ is lower alkyl;
$R^2$ is n-butyl or cyclopentyl;
$R^3$ is methyl;
$R^4$ is

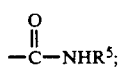

$R^5$ is hydrogen, aralkyl or

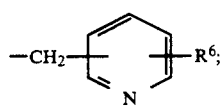

$R^6$ is hydrogen or halo.

The compounds of the invention can be prepared by a basic reaction sequence, in which in the initial step an isovanillin derivative is reacted with a suitable $R^2$ group-containing derivative, to yield an isovanillin derivative intermediate with the appropriately substituted hydroxy group:

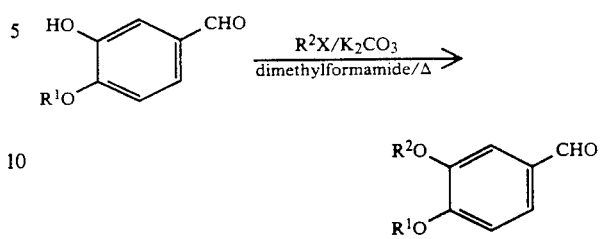

The latter is then reacted with malonic acid in the presence of pyridine and piperidine to yield an intermediate cinnamic acid, which is then reacted with hydrazine hydrate to yield a pyrazolidinone intermediate:

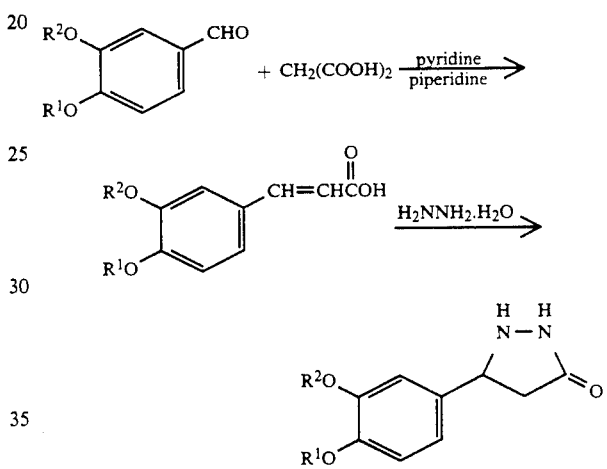

Compounds in which $R^3$ is lower alkyl can be prepared via the above-outlined route by the use of an appropriately substituted hydrazine hydrate:

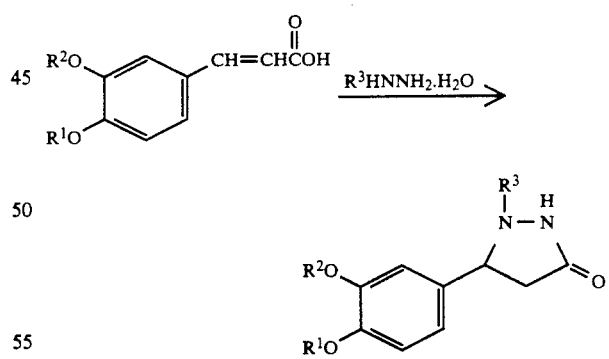

In an alternate sequence, the pyrazolidinone intermediate is reacted with sodium hydride followed by reaction with a suitable $R^3$ derivative in an organic solvent:

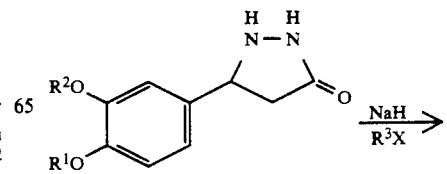

R[4]-substituted pyrazolidinone derivative final products. The following flow chart illustrates the sequences used to prepare the various compounds of the invention:

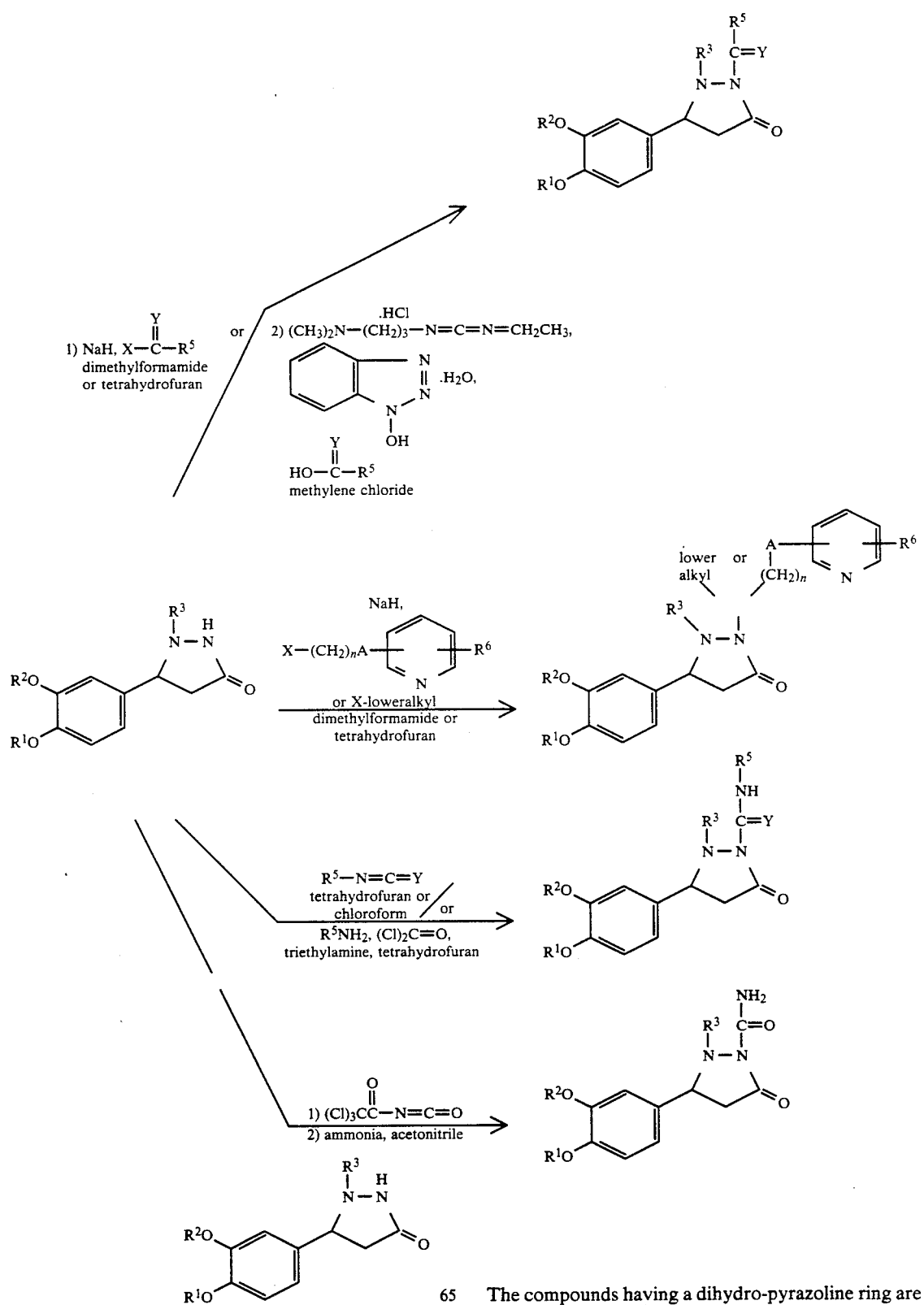

The R[3]-substituted pyrazolidinone compounds are also intermediates for the preparation of the various R[4]-substituted pyrazolidinone derivative final products.

The compounds having a dihydro-pyrazoline ring are likewise prepared from the R[3] substituted pyrazolidinone intermediates according to the following sequence:

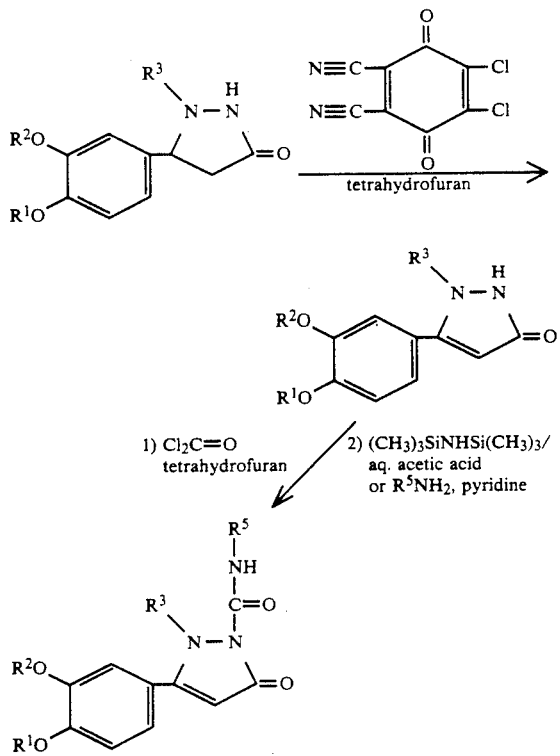

Of course, other methods of preparation, which will occur to those skilled in the art, may also be employed to prepare the compounds of this invention.

The starting materials used in the above-described preparative routes are commercially available, or can be made according to procedures taught in the chemical literature.

Some compounds of the invention possess cis-trans isomerism and chirality and hence the compounds of the invention embrace not only racemic mixtures, but the individual isomers as well. The isomers are designated according to the E/Z-system and the R/S-system using the sequence rule.

The compounds of the invention, by virtue of their ability to inhibit the enzyme 3':5'-cyclic AMP phosphodiesterase of pulmonary tissue (PDE IV) and to inhibit the influx of leukocytes into the lungs and pulmonary cavities, are bronchodilators and antiinflammatories, which are useful in the treatment of acute and chronic bronchial asthma and its associated pathology.

Compounds of the invention which contain a basic nitrogen are capable of forming pharmaceutically acceptable salts, including the salts of pharmaceutically acceptable organic and inorganic acids, such as hydrochloric, hydrobromic, hydroiodic, sulfuric, nitric, phosphoric, methanesulfonic, benzenesulfonic, acetic, citric, pumaric, maleic, succinic and the like.

When the compounds of the invention are employed in the treatment of acute or chronic bronchial asthma, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol. The compounds may also be formulated into dry aerosol inhalation formulations.

The dosage requirements vary with the particular compositions employed, the route of administration, the severity of the symptoms presented and the particular subject being treated. Treatment will generally be initiated with small dosages, less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single dose, or if desired, the dosage may be divided into convenient subunits administered at suitable times throughout the day.

The PDE IV inhibitory effects of the compounds of the invention may be demonstrated by standard pharmacological procedures, which are described more fully in the examples given hereinafter. These procedures illustrate the ability of the compounds of the invention to inhibit PDE IV isolated from canine trachea.

The following examples show the preparation and pharmacological testing of compounds within the invention.

EXAMPLE 1

5-[3-(Cyclopentyloxy)-4-methoxyphenyl]-3-pyrazolidinone

To a suspension of 3-cyclopentyloxy-4-methoxycinnamic acid (7.9 g, 30 mmol) in toluene (25 ml) is added hydrazine hydrate (2.91 ml, 60 mmol). The reaction mixture is heated to 100° (bath temperature) for 24 hours. Toluene is partially removed and ether carefully added, and the product allowed to crystallize. The solid is filtered to give crude product (6 g). A crystallization from chloroform-hexane gives the pure product (5 g) m.p. 185°-186°. $^1$H NMR (CDCl$_3$) δ7.02 (1H, s, NH-CO), 6.88 (3H, m, arom), 4.79 (2H, m, carbinolic and benzylic), 4.28 (1H, m, NH), 3.84 (3H, s, CH$_3$O—), 2.79 (2H, d, —CH$_2$CO), 1.9 (5H, m, cyclopentyl C—H), 1.61 (3H, m, cyclopentyl C—H); IR (KBr), 3420, 3220, 3160, 2960, 1700, 1660 cm$^{-1}$; MS m/z 276 (M)$^+$.

Analysis for: C$_{15}$H$_{20}$N$_2$O$_3$: Calculated: C, 65.22; H, 7.29; N, 10.14. Found: C, 65.45; H, 7.30; N, 9.97.

EXAMPLE 2

5-[3-(Cyclopentyloxy)-4-methoxyphenyl]-1-methyl-3-pyrazolidinone

To a suspension of 3-cyclopentyloxy-4-methoxycinnamic acid (6.3 g, 24 mmol) in toluene (15 ml), is added N-methylhydrazine (3.9 ml, 72 mmol). A precipitate is formed which slowly dissolves on warming. The mixture is kept at 100°-105° (bath temperature) for 24 hours. The solvent is removed under vacuum, and the residue partitioned between ethyl acetate-water. The organic extract is dried and the solvent removed to yield crude product (7.6 g). Filtration through silica gel (100 g) in 50% ethyl acetate/hexane and elution with 70-80% ethylacetate/hexane gives pure product (4 g) m.p. 115°-116°. $^1$H NMR (ME$_2$SO-d$_6$); δ9.44 (1H, s, NHCO), 6.95 (1H, d, arom), 6.88 (2H, m, arom), 4.76 (1H, m, carbinolic), 3.81 (1H, t, benzylic), 3.71 (3H, s, CH$_3$O), 2.76 (1H, 1, —CHCO), 2.36 (3H, s, CH$_3$N), 2.33 (1H, m, —CHCO), 1.86 (2H, m, cyclopentyl—CH), 1.69 (4H, m, cyclopentyl —CH), 1.55 (2H, m, cyclopentyl —CH); IR (KBr); 3425, 3160, 2960, 1690, 1600 cm$^{-1}$. MS m/z; 290 (M)$^+$, 222 (M—C$_5$H$_8$)$^+$, 177 (M—(C$_5$H$_9$+CH$_4$N$_2$))$^+$.

Analysis for: C$_{16}$H$_{22}$N$_2$O$_3$: Calculated: C, 66.20; H, 7.58; N, 9.65. Found: C, 66.05; H, 7.74; N, 9.64.

EXAMPLE 3

5-[3-(Cyclopentyloxy)-4-methoxyphenyl]-1,2-dimethyl-3-pyrazolidinone, hydriodide To a suspension of hexane-washed sodium hydride (0.176 g, 4.4 mmol, 60% suspension), in dry tetrahydrofuran (14 ml), is added 5-[3-(cyclopentyloxy)-4-methoxyphenyl]-3-pyrazolidinone (1.1 g, 4 mmol). The suspension is stirred under nitrogen at room temperature. After 0.5 hours, hydrogen evolution cases and the mixture becomes a turbid solution. Methyl iodide (0.96 ml, 16 mmol) is added at room temperature, and the mixture stirred at room temperature, for 6 hours. The reaction is quenched with water, and the solvent is removed. The residue is suspended in water containing small amount of ethyl acetate. After stirring for about 20 minutes, the solid is filtered to yield crude product (0.6 g). Two crystallizations from methanol-ether yielded a pure sample (0.34 g) m.p. 192.5°-193°. $^1$H NMR (Me$_2$SO-d$_6$) δ7.25 (2H, m, arom), 7.12 (1H, d, arom), 5.57 (1H, q, benzylic), 4.86 (1H, m, carbinolic), 3.8 (3H, s, O—CH$_3$) 3.76 (1H, m, —CHCO), 3.37 (3H, s, CH$_3$N), 3.19 (1H, q, CHCO), 2.94 (3H, s, —CH$_3$N), 1.93 (2H, m, cyclopentyl —CH), 1.70 (4H, m, cyclopentyl—CH), 1.57 (2H, m, cyclopentyl —CH); IR (KBr), 3460, 2970, 1750, 1610 cm$^{-1}$; MS m/z; 305 (M+1)$^+$, 245 (M—C$_2$H$_6$N$_2$+1)$^+$.

Analysis for: C$_{17}$H$_{24}$N$_2$O$_3$: Calculated: C, 47.23; H, 5.83; N, 6.48. Found: C, 47.16; H, 5.61; N, 6.46.

EXAMPLE 4

5-[3-(Cyclopentyloxy)-4-methoxyphenyl]-3-oxo-1-pyrazolidineacetic acid methyl ester To a suspension of hexane-washed sodium hydride (0.264 g, 6.6 mmol, 60% suspension) in tetrahydrofuran (10 ml) is added 5-[3-(cyclopentyloxy)-4-methoxyphenyl]-3-pyrazolidinone (1.66 g, 6 mmol). The mixture is kept at 50° for 30 minutes. To the turbid solution, a solution of methyl bromoacetate (1.53 g, 10 mmol) in tetrahydrofuran (5 ml) is added. The reaction mixture is kept at 60°-70° overnight. The solvent is removed and the residue partitioned between ethyl acetate-water. The organic extract is dried, and the solvent evaporated. The resulting product (2 g) is chromatographed on silica gel (60 g) in 40% ethyl acetate/hexane.

The desired product is eluted with 50-80% ethyl acetate-hexane to yield the product (1.12 g) m.p. 112°-113°. A crystallization from chloroform-hexane yields pure product (0.93 g) m.p. 113°-116°. $^1$H NMR (Me$_2$SO-d$_6$); δ9.47 (1H, s, NH), 6.98 (1H, d, arom), 6.89 (2H, m, arom), 4.75 (1H, m, carbinolic) 4.26 (1H, m, benzylic), 3.7 (3H, s, CH$_3$O), 3.67 (1H, d, —CHCO), 3.6 (3H, s, O —CH$_3$), 3.45 (1H, d, —CHCO), 3.01 (1H, q, —CHCO) 2.28 (1H, q, —CHCO); IR (KBr), 3230, 3140, 2930, 1750, 1735, 1685 cm$^{-1}$; MS m/z 348 (M)$^+$, 289 (M—COOCH$_3$)$^+$, 280 (M—C$_5$H$_9$)$^+$, 221 (280—COOCH$_3$)$^+$.

Analysis for: C$_{18}$H$_{24}$N$_2$O$_5$: Calculated: C, 62.06; H, 6.89; N, 8.04. Found: C, 61.45; H, 6.82; N, 7.99.

EXAMPLE 5

5-[3-(Cyclopentyloxy)-4-methoxyphenyl]-3-oxo-1-pyrazolidinecarboxamide

A suspension of 5-[3-(cyclopentyloxy)-4-methoxyphenyl]-3-pyrazolidinone (1.1 g, 4 mmol) in tetrahydrofuran is cooled to −30° C. Trichloroacetyl isocyanate (0.59 ml, 5 mmol) is added and stirring continued for 45 minutes, during which time the reaction mixture is warmed to room temperature. A saturated solution of ammonia in acetonitrile (5 ml) is added and stirring continued overnight. The solvent is removed, and the residue partitioned between ethyl acetate-water, dried and solvent is evaporated. The resulting residue (1.3 g) is put through silica gel (30 g) in 60% ethyl acetate/hexane and the product eluted with 100% ethyl acetate-20% methanol/ethyl acetate to yield pure compound (0.5 g). Two crystallizations from methanol-ether give analytical sample m.p. 115°-117°. $^1$H NMR (NMe$_2$SO-d$_6$); δ6.96 (1H, d, arom), 6.87 (1H, d, arom), 6.82 (1H, q, arom), 6.47 (2H, b, NH$_2$), 5.49 (1H, d, benzylic), 4.76 (1H, m, carbinolic), 3.72 (3H, s, O—CH$_3$), 3.16 (1H, q, —CHCO), 2.18 (1H, d, —CHCO), 1.90 (2H, m, cyclopentyl —CH), 1.70 (4H, m, cyclopentyl —CH), 1.56 (2H, m, cyclopentyl —CH); IR (KBr), 3380, 3180, 2940, 1660-1700 cm$^{-1}$. MS m/z 319 (M)$^+$, 276 (M—CONH$_2$+1)$^+$, 208 [M—(CONH$_2$+C$_5$H$_8$)+1]$^+$.

Analysis for: C$_{16}$H$_{21}$N$_3$O$_4$: Calculated: C, 60.19; H, 6.58; N, 13.17. Found: C, 60.18; H, 6.12; N, 12.83.

EXAMPLE 6

5-[3-(Cyclopentyloxy)-4-methoxyphenyl]-3-oxo-1-pyrazolidinecarboxylic acid methyl ester To an ice cold suspension of 5-[3-(cyclopentyloxy)-4-methoxyphenyl]-3-pyrazolidinone (0.552 g, 2 mmol) in tetrahydrofuran (3 ml) and triethylamine (0.3 ml, 2.2 mmol) is added methyl chloroformate (0.2 ml, 2.6 mmol). The mixture is stirred at 0° and allowed to reach room temperature. After 2 hours, more methyl chloroformate (0.1 ml, 1.3 mmol) is added, and stirring continued for two more hours. The reaction is quenched with water, solvent is removed, and the residue partitioned between ethyl acetate-water. The organic layer is dried, and solvent is removed to yield crude product (0.6 g). This is purified over silica gel (20 g) in 1:1 ethyl acetate-hexane. The product is eluted with 60-80% ethyl acetate-hexane to give pure product (0.45 g). Crystallization from ethyl acetate-hexane gives analytical sample (0.34 g) m.p. 106°-107°. $^1$H NMR (Me$_2$SO-d$_6$) δ6.92 (1H, d, arom), 6.8 (2H, m, arom), 5.4 (1H, q, benzylic), 4.74 (1H, d, —CHCO), 3.68 (3H, s, O—CH$_3$), 3.64 (3H, s, O—CH$_3$), 3.29 (1H, q, —CHCO), 2.22 (1H, d, —CHCO), 1.86 (2H, m, cyclopentyl —CH), 1.7 (4H, m, cyclopentyl —CH), 1.54 (2H, m, cyclopentyl —CH). IR (KBr); 3570, 2930, 1680, 1710, cm$^{-1}$.

MS m/z; 334 (M)$^+$, 266 (M—C$_5$H$_8$)$^+$.

Analysis for: C$_{17}$H$_{22}$N$_2$O$_5$: Calculated: C, 61.08; H, 6.59; N, 8.38. Found: C, 61.29; H, 6.79; N, 8.49.

EXAMPLE 7

5-[3-(Cyclopentyloxy)-4-methoxyphenyl]-3-oxo-1-pyrazolidinecarboxylic acid

A solution of 5-[3-(cyclopentyloxy)-4-methoxyphenyl]-3-oxo-1-pyrazolidinecarboxylic acid methyl ester (0.696 g, 2 mmol) in methanol (4 ml) is mixed with 2.5N sodium hydroxide solution (1.2 ml, 3 mmol). The reaction mixture is kept at 40° overnight. The solvent is removed, and the residue partitioned between ethyl acetate/water, dried and the solvent evaporated. Residue (0.7 g) is allowed to crystallize over ethyl acetate/ether to yield solid (0.29 g) m.p. 137°–139°. A crystallization from ethyl acetate/ether gives analytical sample m.p. 136°–7°. $^1$H NMR (Me$_2$SO-d$_6$); δ9.38 (1H, broad, NH), 7.02 (1H, d, arom), 6.89 (2H, m, arom), 4.75 (1H, m, carbinolic), 4.27 (1H, q, benzylic), 3.72 (3H, s, O—CH$_3$), 3.60 (1H, d, —CHCO), 3.37 (1H, d, —CHCO), 3.04 (1H, q, —CHCO), 2.25 (1H, q, —CHCO), 1.88 (2H, m, cyclopentyl —CH), 1.70 (4H, m, cyclopentyl —CH), 1.56 (2H, m, cyclopentyl —CH), IR (KBr), 3210, 2940, 2450, 1710, 1630, 1510 cm$^{-1}$.

MS m/z, 335 (M+1)$^+$.

Analysis for: C$_{17}$H$_{22}$N$_2$O$_5$: Calculated: C, 61.08; H, 6.59; N, 8.38. Found: C, 61.18; H, 6.68; N, 8.02.

EXAMPLE 8

3-[3-(Cyclopentyloxy)-4-methoxyphenyl]-2-methyl-5-oxo-pyrazolidinecarboxamide, hydrochloride 5-[3-(Cyclopentyloxy)-4-methoxyphenyl]-1-methyl-3-pyrazolidinone (0.58 g, 2 mmol) is dissolved in tetrahydrofuran (3 ml), and the solution is cooled to −30° C. Trichloroacetyl isocyanate (0.3 ml, 2.5 mmol) is gradually added, and the reaction mixture is stirred and allowed to reach room temperature, during 1 hour. A saturated solution of ammonia in acetonitrile (7 ml) is added to the reaction and stirring continued for three hours. The solvent is removed, and the residue is partitioned between ethyl acetate/water, dried and the solvent is evaporated. The residue (0.9 g) is put on silica gel (13 g) in 20% ethyl acetate/hexane and the product is eluted with 40-50% ethyl acetate/hexane, to yield pure product (0.67 g), as a colorless oil. The product is suspended in ether (~3 ml) and 2N methanolic HCl (3 ml) added to it and the mixture is stirred for 10 minutes. The solvent is removed, the residue triturated with ether, and filtered to yield a white solid (0.61 g). A crystallization from methanol/ether gives analytically pure material (0.42 g) m.p. 142°–143°. $^1$H NMR (Me$_2$SO-d$_6$); δ7.39 (2H, m NH$_2$), 6.97 (1H, d, arom), 6.91 (1H, d, arom), 6.84 (1H, q, arom), 4.71 (1H, m, carbinolic), 4.36 (1H, m, benzylic), 3.70 (3H, s, O—CH$_3$), 3.64 (1H, m, —CHCO), 2.72 (3H, s, N—CH$_3$), 2.64 (1H, m, —CHCO), 1.85 (2H, m, cyclopentyl —CH), 1.67 (4H, m, cyclopentyl —CH), 1.54 (2H, m, cyclopentyl —CH); IR (KBr), 3380, 3250, 2960, 2550, 1790, 1730, 1590 cm$^{-1}$.

MS m/z, 334 (M)$^+$, 291 (M—CONH$_2$+1)$^+$

Analysis for: C$_{17}$H$_{23}$N$_3$O$_4$.HCl: Calculated: C, 55.21; H, 6.47; N, 11.37. Found: C, 55.12; H, 6.43; N, 11.30.

EXAMPLE 9

3-[3-(Cyclopentyloxy)-4-methoxyphenyl]-2-methyl-5-oxo-N-methyl-1-pyrazolidinecarboxamide, hemihydrate 5-[3-(Cyclopentyloxy)-4-methoxyphenyl]-1-methyl-3-pyrazolidinone (0.51 g, 1.75 mmol) is suspended in tetrahydrofuran (3 ml). Methyl isocyanate (0.13 ml, 2.2 mmol) is slowly added to the mixture. The reaction is stirred overnight. More methyl isocyanate (0.065 ml, 1.1 mmol) is added, and the mixture is stirred for 4 hours. The solvent is removed, and the residue partitioned between ethyl acetate/water, dried and solvent is evaporated. The residue (0.7 g) is put through silica gel (20 g) in 30% ethyl acetate/hexane. The product is eluted with 40 to 60% ethyl acetate/hexane to give pure sample (0.58 g) as pale brown oil. The oil (0.3 g) is taken in ether (4 ml) and 2N methanolic HCl (2 ml) added to it. The mixture is stirred for 10 minutes and the solvent is removed. The residue is triturated with ether and filtered to give solid (0.4 g). A crystallization from methanol/ether gives pure sample (0.23 g) m.p. 145°–7° C. Drying for 3 days under vacuum at 60° C. yields a low melting solid (0.2 g), m.p. 65°–68° C. $^1$H NMR (Me$_2$SO-d$_6$); δ7.81 (1H, q, NH), 6.94 (1H, d, arom), 6.89 (1H, d, arom), 6.83 (1H, q, arom), 4.73 (1H, m, carbinolic), 4.36 (1H, m, benzylic), 3.71 (3H, d, O—CH$_3$), 3.63 (1H, m, —CHCO), 2.73 (3H, s, N—CH$_3$), 2.68 (3H, d, N—CH$_3$), 2.62 (1H, m, —CHCO), 1.84 (2H, m, cyclopentyl —CH), 1.62 (6H, m, cyclopentyl —CH).

MS m/z 290 (M—CONHCH$_3$+1)$^+$

Analysis for: C$_{18}$H$_{25}$N$_3$O$_4$.0.5 H$_2$O: Calculated: C, 60.67; H, 7.30; N, 11.8. Found: C, 60.75; H, 7.28; N, 11.7.

EXAMPLE 10

5-[3-(cyclopentyloxy)-4-methoxyphenyl]-1,2-dihydro-1-methyl-3H-pyrazol-3-one To a magnetically-stirred solution of 5-[3-(cyclopentyloxy)-4-methoxyphenyl]-1-methyl-3-pyrazolidinone (68.88 mmol, 20.0 g) in dry tetrahydrofuran (300 mL) at 0° C. is added, via cannula, a suspension of 2,3-dichloro-5,6-dicyano-1,4-benzoquinone (DDQ, 68.88 mmol, 15.64 g) in 200 mL dry tetrahydrofuran. The resulting heterogeneous mixture is allowed to warm slowly from 0° C. to room temperature overnight. The solvent is removed in vacuo and the reddish-brown residue is triturated with methylene chloride. The undissolved yellow solid is removed via suction and discarded. The filtrate is concentrated in vacuo to produce a brownish foam which is purified by flash chromatography (SiO$_2$: gradient ranging from 15% ethyl acetate/methylene chloride to 30% ethyl acetate/methylene chloride). Concentration in vacuo affords a light tan solid which is dried overnight in vacuo at 50° C. to give the title compound (22.54 mmol, 6.50 g., 32.7%). $^1$H NMR (DMSO-d$_6$, 400 MHz) δ9.58 (s, 1H); 6.98 (m, 3H); 5.53 (s, 1H); 4.83 (m, 1H); 3.77 (s, 3H); 3.60 (s, 3H); 1.90 (m, 2H); 1.70 (m, 4H); 1.55 (m, 2H). IR (KBr, cm$^{-1}$) 3440, 2950, 2830, 1950, 1600, 1517, 1483, 1310, 1252, 1235, 1165, 1135, 1020, 770.

MS (EI, m/e(%)) 228 (6, M+); 220 (38); 185 (56); 168 (28); 153 (29); 143 (33); 127 (100); 115 (38); 77 (19).

Analysis for: C$_{16}$H$_{20}$N$_2$O$_3$: Calculated: C, 66.64; H, 6.99; N, 9.72. Found: C, 66.23; H, 6.62; N, 9.53.

EXAMPLE 11

3-[3-(cyclopentyloxy)-4-methoxyphenyl]-2,5-dihydro-2-methyl-5-oxo-1H-pyrazole-1-carboxamide To a 0° C. solution of phosgene (8.75 mmol, 4.61 mL; 1.9M solution in toluene) in dry tetrahydrofuran (30 mL) is added 5-[3-(cyclopentyloxy)-4-methoxyphenyl]-1,2-dihydro-1-methyl-3H-pyrazol-3-one (7.0 mmol, 2.02 g) in dry tetrahydrofuran (15 mL) dropwise over 20 minutes. The resulting cloudy solution is stirred at 0° C.

for 10 minutes and at room temperature for 1 hour after which a homogenous solution is obtained. The reaction mixture is cooled to 0° C. and hexamethyldisilazane (17.5 mmol, 2.82 g; 3.64 mL) in dry tetrahydrofuran (15 mL) is added in one portion. The resulting suspension is stirred at room temperature for 1 hour and then the volatiles are removed in vacuo. The residue is partitioned between 2% aqueous acetic acid (200 mL) and ethyl acetate (200 mL) and the aqueous phase is extracted with ethyl acetate (150 mL). The combined organic layers are washed with H$_2$O (100 mL), dried (Na$_2$SO$_4$), and concentrated in vacuo to afford a tan solid. This material is triturated with ether and dried in vacuo for 1 hour at 60° C. to give the title compound as a white solid (1.80 g; 78%). $^1$H NMR (DMSO-d$_6$, 400 MHz) δ7.23 (br s, 1H); 7.02 (m, 3H); 6.92 (br s, 1H); 6.08 (s, 1H); 4.86 (m, 1H); 3.78 (s, 3H); 3.72 (s, 3H); 1.88 (m, 2H); 1.70 (m, 4H); 1.56 (m, 2H). IR (KBr, cm$^{-1}$) 3400, 3300, 3200, 2950, 1760, 1500, 1330, 1250, 1130.

MS (+FAB, m/e (%)) 332 (90, M+H); 289 (100); 220 (40).

Analysis for: C$_{17}$H$_{21}$N$_3$O$_4$: Calculated: C, 61.62; H, 6.39; N, 12.68. Found: C, 61.67; H, 6.35; N, 12.30.

EXAMPLE 12

3-[3-(cyclopentyloxy)-4-methoxyphenyl]-2,5-dihydro-2-methyl-5-oxo-N-(2-pyridinylmethyl)-1H-pyrazole-1-carboxamide In the same manner as Example 11 above, 5-[3-(cyclopentyloxy)-4-methoxyphenyl]-1,2-dihydro-1-methyl-3H-pyrazol-3-one (0.8 mmol, 0.230 g) in tetrahydrofuran (5 mL) was reacted with phosgene (1.00 mmol, 0.526 mL; 1.9M solution in toluene) in tetrahydrofuran (5 mL) and to this solution was added 2-(methylamino)-pyridine (1.00 mmol, 0.108 g; 0.103 mL) and pyridine (2.00 mmol, 0.158 g; 0.162 mL) in tetrahydrofuran (5 mL) in one portion at 0° C. The resulting yellow suspension is stirred for 1 hour at room temperature, and the resulting dark red reaction mixture is partitioned between ethyl acetate (100 mL) and water (100 mL). The aqueous phase is extracted with ethyl acetate (100 mL), the combined organic layers are washed with water (100 mL), dried (Na$_2$SO$_4$), and concentrated in vacuo to afford a dark brown residue. This material is purified by flash chromatography (SiO$_2$: 1) methylene chloride; 2) 5% ethyl acetate/methylene chloride; 3) 10% ethyl acetate/methylene chloride) to give a light brown oil. Treatment with ether and ethanolic HCl yields the title compound as the dihydrochloride salt which is dried in vacuo at 60° C. for 2 hours (100 mg; 25%). $^1$H NMR (DMSO-d$_6$, 400 MHz) δ8.75 (d, 1H, J=5 Hz); 8.62 (t, 1H, J=5 Hz); 8.33 (t, 1H, J=7 Hz); 7.76 (m, 2H); 7.02 (m, 3H), 6.13 (s, 1H); 4.86 (m, 1H); 4.58 (d, 2H, J=6 Hz); 3.78 (s, 3H); 3.73 (s, 3H); 1.88 (m, 2H); 1.72 (m, 4H); 1.55 (m, 2H). IR (KBr, cm$^{-1}$) 3400, 3225, 2950, 2575, 2400, 1780, 1750, 1615, 1395, 1360, 1255.

MS (+FAB, m/e (%)) 423 (10, M+H); 289 (100); 135 (40).

Analysis for: C$_{23}$H$_{26}$N$_4$O$_4$.2 HCl.0.35 H$_2$O: Calculated: C, 55.06; H, 5.77; N, 11.17. Found: C, 55.08; H, 5.74; N, 11.20.

EXAMPLE 13

(S)-3-[3-(cyclopentyloxy)-4-methoxyphenyl]-2-methyl-N-[1-(1-naphthalenyl)ethyl]-5-oxo-1-pyrazolidine carboxamide To a stirred solution of 5-[3-(cyclopentyloxy)-4-methoxyphenyl]-1-methyl-3-pyrazolidinone (2.0 mmol, 0.580 g) in dry tetrahydrofuran (10 mL) at 0° C. is added neat (S)-(+)-1-(1-naphthyl)ethyl isocyanate in one portion. The resulting colorless solution is stirred at room temperature overnight and the volatiles are removed in vacuo. The residue is partitioned between ethyl acetate (200 mL) and water (200 mL) and the aqueous phase is extracted with ethyl acetate (1×100 mL). The combined organic layers are dried (Na$_2$SO$_4$) and concentrated in vacuo. The residue is purified by flash chromatography (SiO$_2$: 1) methylene chloride; 2) 2% ethyl acetate/methylene chloride; 3) 5% ethyl acetate/methylene chloride) to afford the diastereomerically-pure products as white solids. In this experiment, one obtains 0.450 g (46%) of high R$_f$ diastereomer and 0.460 g (47%) of low R$_f$ diastereomer.

A) high R$_f$ diastereomer $^1$H NMR (DMSO-d$_6$, 400 MHz) δ8.38 (d, 1H, J=8 Hz); 8.12 (d, 1H, J=8 Hz); 7.96 (dd, 1H, J=8, 1.5 Hz); 7.85 (t, 1H, J=5 Hz); 7.55 (m, 2H), 7.49 (d, 2H, J=4.5 Hz); 6.97 (d, 1H, J=2 Hz); 6.89 (d, 1H, J=8 Hz); 6.84 (dd, 1H, J=8, 2 Hz); 5.71 (p, 1H, J=7 Hz); 4.72 (m, 1H); 4.38 (m, 1H); 3.72 (s, 3H); 3.65 (m, 1H); 2.72 (s, 3H); 2.70 (m, 1H); 1.88 (m, 2H); 1.67 (m, 4H); 1.55 (m, 5H). IR (KBr, cm$^{-1}$) 3400, 3300, 2950, 1715, 1700, 1505, 1300, 1250, 1220, 770.

MS (+FAB, m/e (%)) 488 (10, M+H); 313 (20); 291 (100); 177 (25); 155 (90).

Analysis for: C$_{29}$H$_{33}$N$_3$O$_4$: Calculated: C, 71.44; H, 6.82; N, 8.62. Found: C, 71.10; H, 6.89; N, 8.26.

Optical Rotation (MeOH, 10.1 mg/mL) α=−0.053-°|α|$_D$=−5.2°

B) low R$_f$ diastereomer $^1$H NMR (DMSO-d$_6$, 400 MHz) δ8.44 (d, 1H, J=8 Hz); 8.12 (d, 1H, J=8 Hz); 7.95 (d, 1H, J=8 Hz); 7.83 (d, 1H, J=8 Hz); 7.55 (m, 2H); 7.44 (m, 2H); 6.90 (d, 1H, J=2 Hz); 6.84 (d, 1H, J=8 Hz); 6.79 (dd, 1H, J=8, 2 Hz); 5.75 (p, 1H, J=7 Hz); 4.50 (m, 1H); 4.38 (m, 1H); 3.72 (m, 1H); 3.68 (s, 3H); 2.76 (s, 3H); 2.63 (m, 1H); 1.70 (m, 1H); 1.57 (d, 3H, J=7 Hz); 1.49 (m, 5H); 1.34 (m, 1H), 1.23 (m, 1H). IR (KBr, cm$^{-1}$) 3400, 3300, 2960, 1715, 1965, 1505, 1250, 1220.

MS (CI, m/e (%)) 488 (15, M+H); 445 (60); 291 (100); 197 (95); 155 (98).

Analysis for: C$_{29}$H$_{33}$N$_3$O$_4$: Calculated: C, 71.44; H, 6.82; N, 8.62. Found: C, 71.21; H, 6.81; N, 8.55.

Optical Rotation (MeOH, 9.2 mg/mL) α=+0.837-°|α|$_D$=+91.0°

EXAMPLE 14

N-butyl-3-[3-(cyclopentyloxy)-4-methoxyphenyl]-2-methyl-5-oxo-1-pyrazolidinecarboxamide hydrochloride 5-[3-(cyclopentyloxy)-4-methoxyphenyl]-1-methyl-3-pyrazolidinone (2.06 mmol, 0.600 g) is dissolved in dry chloroform (10 mL) in a N$_2$ atmosphere. To this is added dropwise at room temperature butyl isocyanate (5.15 mmol; 0.583 mL) neat. The sample is heated to reflux for 4 hours at which time TLC shows no starting material. The sample is evaporated to yield a clear oil which is dissolved in ether. To this solution is added ethanolic HCl and the sample is stirred for 15 minutes and evaporated in vacuo to afford a solid which is recrystallized from chloroform and hexane to give the title compound as a white solid (0.495 mg; 56%) m.p.:

115°–122° C. (dec) $^1$H NMR (DMSO-d$_6$, 400 MHz) δ8.3 (s, 1H); 7.91 (t, 3H, J=5.7 Hz); 6.95 (d, 1H, J=1.3 Hz); 6.89 (d, 1H, J=8.3 Hz); 6.81 (dd, 1H, J=8.3, 1.6 Hz); 4.68 (m, 1H); 4.35 (d, 1H, J=5.6 Hz); 3.69 (s, 3H); 3.15 (m, 2H); 2.73 (s, 3H); 1.84 (m, 2H); 1.68 (m, 3H); 1.54 (m, 2H); 1.40 (m, 2H); 1.23 (m, 3H); 0.85 (t, 2H, J=7.3 Hz). IR (KBr, cm$^{-1}$) 1760

MS (EI, m/e) 389 (M+); 290.

Analysis for: C$_{21}$H$_{31}$N$_3$O$_4$.HCl: Calculated: C, 59.22; H, 7.57; N, 9.86. Found: C, 58.92; H, 7.68; N, 9.72.

EXAMPLE 15

3-[3-(cyclopentyloxy)-4-methoxyphenyl]-N-ethyl-2-methyl-5-oxo-1-pyrazolidinecarboxamide hydrochloride, hydrate Following the procedure of Example 14 and using ethyl isocyanate, yields 40% of title compound. m.p.: 106°–111° C. $^1$H NMR (DMSO-d$_6$, 400 MHz) δ7.91 (t, 3H, J=5.7 Hz); 6.95 (d, 1H, J=1.6 Hz); 6.89 (d, 1H, J=8.3 Hz); 6.83 (dd, 1H, J=8.3, 1.6 Hz); 4.69 (m, 1H); 4.36 (d, 1H, J=6 Hz); 3.69 (s, 3H); 3.17 (m, 2H); 2.72 (s, 3H); 1.68 (m, 2H); 1.66 (m, 3H); 1.53 (m, 2H). IR (KBr, cm$^{-1}$) 1770, 1720.

MS (EI, m/e) 361 (M+); 290.

Analysis for: C$_{19}$H$_{28}$N$_3$O$_4$.HCl.H$_2$O: Calculated: C, 54.73; H, 7.49; N, 10.07. Found: C, 54.89; H, 7.18; N, 10.05.

EXAMPLE 16

3-[3-(cyclopentyloxy)-4-methoxyphenyl]-2-methyl-5-oxo-N-phenyl-1-pyrazolidine carboxamide hydrochloride Following the procedure of Example 14 and using phenyl isocyanate, yields 0.850 g (93%) of title compound as a white powder. m.p.: 134°–142° C. (dec) $^1$H NMR (DMSO-d$_6$, 400 MHz) δ9.95 (s, 1H); 7.50 (d, 2H, J=9 Hz); 7.32 (t, 2H, J=7 Hz); 7.08 (t, 1H, J=7 Hz); 7.00 (s, 1H); 6.90 (m, 2H); 4.70 (m, 1H); 3.69 (s, 3H); 2.80 (m, 4H); 1.82 (m, 2H); 1.64 (m, 3H); 147 (m, 2H). Br, cm$^{-1}$) 1760, 1730.

MS (+FAB, m/e) 410 (M+H).

EXAMPLE 17

3-[3-(cyclopentyloxy)-4-methoxyphenyl]-2-methyl-5-oxo-N-(phenylmethyl)-1-pyrazolidinecarboxamide hydrochloride Following the procedure of Example 14 and using benzyl isocyanate, yields 0.275 g (35%) of title compound as a light yellow solid. m.p.: 67°–72° C. (dec) $^1$H NMR (DMSO-d$_6$, 400 MHz) δ8.36 (m, 1H); 7.26 (m, 5H); 6.95 (s, 1H); 6.86 (m, 2H); 4.65 (m, 1H); 4.37 (m, 3H); 3.70 (s, 3H); 2.74 (s, 3H), 1.80 (m, 2H); 1.64 (m, 3H); 1.50 (m, 2H). IR (KBr, cm$^{-1}$) 1760, 1720.

MS (EI, m/e) 423 (M+).

Analysis for: C$_{24}$H$_{29}$N$_3$O$_4$.0.5 HCl: Calculated: C, 65.68; H, 6.60; N, 9.49. Found: C, 65.68; H, 6.76; N, 9.36.

EXAMPLE 18

N-cyclohexyl-3-[3-(cyclopentyloxy)-4-methoxyphenyl]-2-methyl-5-oxo-1-pyrazolidine carboxamide hydrochloride Following the procedure of Example 14 and using cyclohexyl isocyanate, yields 0.270 g (16%) of title compound as a white solid. mp: 105°–110° C. (dec) $^1$H NMR (DMSO-d$_6$, 400 MHz) δ7.88 (d, 1H, J=7 Hz); 6.94 (d, 1H, J=2 Hz); 6.89 (d, 1H, J=8 Hz); 6.81 (dd, 1H, J=8, 2 Hz); 4.67 (m,1H); 4.36 (d, 1H, J=7 Hz); 3.69 (s, 3H); 2.48 (m, 4H); 1.70 (m, 13H); 1.26 (m, 5H). IR (KBr, cm$^{-1}$) 1760, 1720.

MS (EI, m/e) 416 (M+).

Analysis for: C$_{23}$H$_{33}$N$_3$O$_4$.0.5 HCl: Calculated: C, 63.68; H, 7.66; N, 9.68. Found: C, 63.06; H, 7.77; N, 9.48.

EXAMPLE 19

3-[3-(cyclopentyloxy)-4-methoxyphenyl]-N-(4-methoxyphenyl)-2-methyl-5-oxo-1-pyrazolidinecarboxamide Following the procedure of Example 14 and using 4-methoxyphenyl isocyanate, yields 0.525 g (70%) of title compound as a white solid. m.p.: 123°–125° C. $^1$H NMR (CDCl$_3$, 400 MHz) δ9.98 (s, 1H); 7.42 (d, 2H, J=9 Hz); 7.26 (s, 1H); 7.00 (d, 1H, J=2 Hz); 6.87 (m, 3H); 4.78 (m, 1H); 4.39 (br s, 1H); 3.82 (s, 3H); 3.79 (s, 3H); 1.83 (m, 6H); 1.58 (m, 2H). IR (KBr, cm$^{-1}$) 1720, 1710.

MS (+FAB, m/e) 440 (M+H).

Analysis for: C$_{24}$H$_{29}$N$_3$O$_5$: Calculated: C, 65.59; H, 6.65; N, 9.56. Found: C, 65.26; H, 6.72; N, 9.49.

EXAMPLE 20

3-[3-(cyclopentyloxy)-4-methoxyphenyl]-N-[(4-fluorophenyl)methyl]-2-methyl-5-oxo-1-pyrazolidinecarbothioamide Following the procedure of Example 14 above, 4-fluorobenzyl isothiocyanate yielded 0.146 g (19%) of title compound as a white solid. mp: 48°–51° C. $^1$H NMR (CDCl$_3$, 400 MHz) δ10.38 (s, 1H); 7.28 (m, 2H); 7.18 (s, 1H); 7.02 (t, 2H, J=8 Hz); 6.84 (m, 2H); 4.82 (d, 3H, J=5 Hz); 4.43 (m, 1H); 3.83 (s, 3H); 1.88 (m, 5H); 1.60 (m, 3H). IR (film, cm$^{-1}$) 1700.

MS (+FAB, m/e) 458 (M+H).

Analysis for: C$_{24}$H$_{28}$FN$_3$O$_3$S: Calculated: C, 63.00; H, 6.17; N, 9.18. Found: C, 63.13; H, 6.25; N, 9.45.

EXAMPLE 21

3-[3-(cyclopentyloxy)-4-methoxyphenyl]-N-[(4-methoxyphenyl)methyl]-2-methyl-5-oxo-1-pyrazolidinecarbothioamide Following the procedure of Example 14 and using 4-methoxybenzyl isothiocyanate, yielded 0.489 g (63%) of title compound as a yellow solid. m.p.: 52°–55° C. $^1$H NMR (DMSO-d$_6$, 400 MHz) δ10.28 (m, 1H); 7.22 (d, 2H, J=9 Hz); 7.13 (d, 1H, J=2 Hz); 6.88 (m, 4H); 4.70 (m, 2H); 4.48 (d, 1H, J=8 Hz); 3.70 (s, 3H); 3.69 (s, 3H); 1.72 (m, 7H). IR (KBr, cm$^{-1}$) 1700.

MS (+FAB, m/e) 470 (M+H).

Analysis for: C$_{24}$H$_{31}$N$_3$O$_4$S: Calculated: C, 63.00; H, 6.83; N, 9.18. Found: C, 63.94; H, 6.53; N, 8.66.

EXAMPLE 22

3-[3-(cyclopentyloxy)-4-methoxyphenyl]-N-(4-fluorophenyl)-2-methyl-5-oxo-1-pyrazolidinecarboxamide Following the procedure of Example 14 above, 4-fluorophenyl isocyanate yielded 0.375 g (43%) of title compound as white needles. m.p.: 123°–124° C. $^1$H NMR (CDCl$_3$, 400 MHz) δ10.06 (s, 1H); 7.50 (m, 2H); 7.26 (s, 1H); 7.02 (m, 3H); 6.86 (m, 2H); 4.77 (m, 1H); 4.39 (m, 1H); 3.82 (s, 3H); 3.50 (m, 1H); 2.90 (m, 4H); 1.85 (m, 5H); 1.58 (m, 3H). IR (KBr, cm$^{-1}$) 1720, 1710.

MS (CI, m/e) 428 (M+H).

Analysis for: C$_{23}$H$_{25}$FN$_3$O$_4$: Calculated: C, 64.78; H, 5.91; N, 9.85. Found: C, 64.45; H, 6.20; N, 9.67.

EXAMPLE 23

3-[3-(cyclopentyloxy)-4-methoxyphenyl]-5-oxo-2-(phenylmethyl)-1-pyrazolidinecarboxamide 3-[3-(cyclopentyloxy)-4-methoxyphenyl]-1-(phenylmethyl)-pyrazolidinone (0.994 gms, 2.71 mmol) is dissolved in tetrahydrofuran (4.07 mls) and cooled to 0° C. under $N_2$. Trichloroacetyl isocyanate (0.421 mls, 3.39 mmol, 1.25 eq) is added and the solution is stirred. After one hour the ice bath is removed, and saturated ammonia in acetonitrile (22.5 mls) is added at room temperature. After two hours, solvents are removed in vacuo. The residue is diluted with ethyl acetate (45 mls) and washed with water (45 mls). The aqueous layer is extracted with ethyl acetate (45 mls) and the combined organics are dried over $Na_2SO_4$. The crude product is chromatographed [hexane, 4:1, 3:2, 1:1 (hexane:ethyl acetate)] and recrystallized (methylene chloride/hexane) to afford the title compound as a white solid (0.747 gms, 1.82 mmol, 67%, m.p. 148°-149° C.) $^1$H NMR (DMSO-$d_6$, 400 MHz) δ7.52 (s, 1H), 7.50–6.77 (m, 8H), 7.41 (s, 1H), 4.63 (m, 1H), 4.27 (m, 1H), 4.16 (m, 2H), 3.67 (s, 3H), 3.58 (m, 1H), 2.49 (m, 2), 1.86–1.53 (m, 8H). IR(KBr, cm$^{-1}$) 3380, 3360, 1725(C=O), 1700(C=O). MS(FAB), m/z 410 (MH+).

Analysis for: $C_{23}H_{27}N_3O_4$: Calculated: C, 67.46; H, 6.65; N, 10.26. Found: C, 67.41; H, 6.67; N, 10.32.

EXAMPLE 24

3-[3-(cyclopentyloxy)-4-methoxyphenyl]-2-methyl-5-oxo-N-(3-pyridinylmethyl)-1-pyrazolidine carboxamide To a −15° C. solution of phosgene (4.50 mmol, 2.30 mL; 1.9M solution in toluene) in dry tetrahydrofuran (8 mL) is added neat triethylamine (4.50 mmol, 0.450 g; 0.620 mL) and the resulting suspension is stirred at −15° C. for 10 minutes. To this suspension is added 3-picolylamine (4.50 mmol, 0.490 g; 0.460 mL) and triethylamine (4.50 mmol, 0.450 g; 0.620 mL) in dry tetrahydrofuran (10 mL) in one portion and the reaction mixture is stirred at −15° C. for 30 minutes. Subsequently, 5-[3-(cyclopentyloxy)-4-methoxyphenyl]-1-methyl-3-pyrazolidinone (3.0 mmol, 0.870 g) in dry tetrahydrofuran (7 mL) is added at −15° C. and the reaction mixture is allowed to warm to room temperature overnight. The reaction is quenched with water (20 mL), the volatiles removed in vacuo, and the residue partitioned between ethyl acetate (150 mL) and water (150 mL). The organic layer is dried ($Na_2SO_4$) and concentrated in vacuo to give a tan solid. This material is purified by flash chromatography ($SiO_2$:1) 50% ethyl acetate/hexane; 2) 100% ethyl acetate; 3) 5% methanol/ethyl acetate) to give a mixture of starting material and product which is triturated with ether. The title compound is isolated as a white solid (0.158 g; 12%). Also isolated is a mixture of starting pyridazone and title compound (0.511 g). $^1$H-NMR (DMSO-$d_6$, 400 MHz) δ8.45 (m, 3H); 7.65 (dt, 1H, J=8.0, 1.6 Hz); 7.22 (ddd, 1H, J=8.0, 5.0, 0.7 Hz); 6.94 (d, 1H, J=2.0 Hz); 6.88 (d, 1H, J=8.0 Hz); 6.82 (dd, 1H, J=8.0, 2.0 Hz); 4.63 (m, 1H); 4.38 (m, 3H); 3.70 (s, 3H); 3.65 (m, 1H); 2.74 (s, 3H); 2.65 (m, 1H); 1.79 (m, 2H); 1.63 (m, 4H); 1.49 (m, 2H). IR (KBr, cm$^{-1}$) 3420, 3320, 2950, 1730, 1715, 1530, 1515, 1235, 1135.

MS (CI, m/e (%)) 425(M+, 55), 291(100), 135(99).

Analysis for: $C_{23}H_{28}N_4O_4$: Calculated: C, 65.08; H, 6.65; N, 13.20. Found: C, 64.75; H, 6.67; N, 13.14.

EXAMPLE 25

5-[3-(cyclopentyloxy)-4-methoxyphenyl]-1-methyl-2-(3-pyridinylmethyl)-3-pyrazolidinone hydrochloride dihydrate Sodium hydride (0.14 g of a 60% dispersion in mineral oil, 3.5 mmol, 1.0 equiv) is added to a solution of 5-[3-(cyclopentyloxy)-4-methoxyphenyl]-1-methyl-3-pyrazolidinone (1.0 g, 3.4 mmol, 1.0 equiv) in anhydrous N,N-dimethylformamide (20 mL), and the reaction mixture is stirred at room temperature for 20 minutes. 3-Picolyl chloride (0.54 g, 4.2 mmol, 1.2 equiv) in N,N-dimethylformamide is added dropwise and the resulting mixture is stirred at room temperature for 48 hours. The solvent is removed in vacuo and the residue is taken up in methylene chloride, washed once with 1N sodium hydroxide, once with brine, and then dried ($Na_2SO_4$). Chromatography on silica gel with hexanes/ethyl acetate gives 0.7 g of an oil, which is dissolved in 2N HCl (0.9 mL) and methanol. Evaporation and recrystallization from ethyl acetate and methylene chloride yields 0.16 g (12%) of a white solid identified as 5-[3-(cyclopentyloxy)-4-methoxyphenyl]-1-methyl-2-(3-pyridinylmethyl)-3-pyrazolidinone hydrochloride dihydrate: mp 182°-186° C. $^1$H NMR ($d^6$-DMSO, 400 MHz) δ8.83 (d, J=5.0 Hz, 1H), 8.80 (s, 1H), 8.33 (d, J=8 Hz, 1H), 7.93 (dd, J=5, 8 Hz, 1H), 6.79 (d, J=8 Hz, 1H), 6.76 (d, J=2 Hz, 1H), 6.68 (d, J=8 Hz, 1H), 4.96 (AB quartet, J=16 Hz, 1H), 4.62 (m, 1H), 4.59 (AB quartet, J=16 Hz, 1H), 4.06 (m, 1H), 3.70 (s, 3H), 3.11 (m, 1H), 2.69 (m, 1H), 2.53 (s, 3H), 1.87-1.48 (m, 8H). IR (KBr, cm$^{-1}$) 3420, 3005, 2942, 2920, 2580, 2260, 1725, 1600, 1540, 1510, 1460, 1355, 1335, 1242, 1157.

MS, m/e (relative intensity) 381 (M+, 55), 289 (100), 221 (54), 150 (58).

Analysis for: $C_{22}H_{32}ClN_3O_5$: Calculated: C, 58.34; H, 7.12; N, 9.27. Found: C, 57.72; H, 6.43; N, 9.05.

EXAMPLE 26

5-[3-(cyclopentyloxy)-4-methoxyphenyl]-2-heptyl-1-methyl-3-pyrazolidinone hydrochloride Following the general procedure of Example 25, the reaction of bromoheptane (0.65 mL, 4.1 mmol, 1.2 equiv) in dimethylformamide gives after chromatography on silica gel with hexanes/ethyl acetate, 0.7 g of an oil, which is dissolved in 2N HCl (0.9 mL) and methanol. Evaporation and recrystallization from ethyl acetate and hexanes yields 0.56 g (43%) of a white solid identified as 5-[3-(cyclopentyloxy)-4-methoxyphenyl]-2-heptyl-1-methyl-3-pyrazolidinone hydrochloride: mp 113°-117° C.

$^1$H NMR ($d^6$-DMSO, 400 MHz) δ6.96 (s, 1H), 6.89 (m, 2H), 4.74 (m, 1H), 4.06 (m, 1H), 3.71 (s, 3H), 3.54 (dt, J=7, 14 Hz, 1H), 3.10 (m, 1H), 3.03 (dd, J=7, 16 Hz, 1H), 2.52 (s, 3H), 2.50 (m, 1H), 1.84 (m, 2H), 1.70 (m, 4H), 1.61-1.42 (m, 4H), 1.18 (m, 8H), 0.83 (t, J=7 Hz, 3H). IR (KBr, cm$^{-1}$) 3420, 2940, 2919, 2840, 2220, 1730, 1710, 1600, 1582, 1510, 1440, 1260, 1160, 1140.

MS m/e (relative intensity) 388 (M+, 100), 320 (16), 177 (85), 150 (59).

Analysis for: $C_{23}H_{37}ClN_2O_3$: Calculated: C, 65.00; H, 8.77; N, 6.59. Found: C, 65.01; H, 8.66; N, 6.53.

EXAMPLE 27

2-[(5-bromo-3-pyridinyl)methyl]-5-[3-(cyclopentyloxy)-4-methoxyphenyl]-1-methyl-3-pyrazolidinone hydrochloride

A. 5-bromo-3-(bromomethyl)pyridine

To a solution of 5-bromo-3-pyridylmethanol [see Kauffman, T., and Fischer, H.(1973) Chem. Ber. 106, 220–227.] (0.525 gms, 2.79 mmol) in methylene chloride (2.6 mls) at 0° C. is added pyridine (0.26 mls, 3.21 mmol) then mesyl chloride (0.25 mls, 3.23 mmol). After stirring 2 hours, $K_2CO_3$ (0.88 gms, 6.37 mmol) is added. Stirring is continued for one hour and the ice bath is removed. The mixture is diluted with methylene chloride and washed with saturated aqueous $NaHCO_3$. The organic layer is dried over $Na_2SO_4$ and evaporated to a viscous residue (>0.6 gms). The residue is dissolved in methylene chloride (8.8 mls) and tetrahydrofuran (4.4 mls) without further purification or characterization. LiBr powder (0.46 gms, 5.53 mmol) is introduced and the reaction is immersed in an oil bath (80° C.) for one hour. The crude mixture is concentrated and resolvated with ethyl acetate. Any remaining residue is pulverized and rinsed with methylene chloride. Combined organics are dried over $Na_2SO_4$ and evaporated to a solid (0.7 gms, 2.79 mmol; 100%). $^1H$ NMR ($CDCl_3$, 300 MHz) $\delta 8.65$ (s, 1H), 8.55 (s, 1H), 7.90 (s, 1H), 4.45 (s, 2H).

B. 2-[(5-bromo-3-pyridinyl)methyl]-5-[3-(cyclopentyloxy)-4-methoxyphenyl]-1-methyl-3-pyrazolidinone hydrochloride To a solution of 5-[3-(cyclopentyloxy)-4-methoxyphenyl]-1-methyl-3-pyrazolidinone (0.81 gms, 2.79 mmol) in dimethylformamide (16 mls) is added NaH (0.11 gms, 60%, 2.75 mmol) at room temperature. After stirring 15 minutes, 5-bromo-3-(bromomethyl)pyridine (0.70 gms, 2.79 mmol) is added and the solution is immersed in an oil bath (75° C.). After 20 hours, dimethylformamide is removed in vacuo. The crude material (0.9 gms) is chromatographed (1:1 hexane:ethyl actate, then 2:1 ethyl acetate:hexane) and dissolved in methanol (10 mls), then 0.7 mls 2N HCl is added. The resulting mixture is evaporated and resolvated (methanol) twice to yield the salt (0.65 gms, 1.31 mmol, 47%). Recrystallization in methylene chloride/ethyl acetate affords 0.12 gms of solid title compound (mp 163°–164°). $^1H$ NMR (DMSO-$d_6$, 400 MHz) $\delta 8.60$ (s, 1H), 7.80 (s, 1H), 6.80 (d, J=8.2 Hz, 1H), 6.75 (s, 1H), 6.65 (d, J=9.2 Hz, 1H), 4.80 (d, J=16.0 Hz, 1H), 4.55 (m, 1H), 4.35 (d, J=16.1 Hz, 1H), 4.05 (m, 1H), 3.70 (s, 3H), 3.10 (m, 2H), 2.55 (s, 3H), 1.65 (m, 8H). IR (KBr, cm$^{-1}$) 1690 (C=O).

MS, m/z 460 (M+).

Analysis for: $C_{22}H_{26}N_3O_3Br \cdot HCl$: Calculated: C, 53.19; H, 5.48; N, 8.46. Found: C, 52.84; H, 5.64; N, 8.33.

EXAMPLE 28

5-[3-(cyclopentyloxy)-4-methoxyphenyl]-1-methyl-2-(5-bromo-3-pyridinylcarbonyl)-3-pyrazolidinone Following the general procedure of Example 25, the reaction of 5-bromonicotinyl chloride (from 2 g of 5-bromonicotinic acid, which is treated with oxalyl chloride/dimethylformamide in benzene, 9.9 mmol, 1.4 equiv) in tetrahydrofuran gives, after recrystallization from hexanes and methylene chloride, 0.7 g (21%) of a white solid identified as 5-[3-(cyclopentyloxy)-4-methoxyphenyl]-1-methyl-2-(5-bromo-3-pyridinylcarbonyl)-3-pyrazolidinone: mp 139°–141° C. $^1H$ NMR ($d^6$-DMSO, 400 MHz) $\delta 8.83$ (d, J=2 Hz, 1H), 8.65 (d, J=2 Hz, 1H), 8.17 (t, J=2 Hz, 1H), 7.00 (s, 1H), 6.93 (s, 2H), 4.76 (m, 1H), 4.42 (t, J=7 Hz, 1H), 3.72 (s, 3H), 3.39 (dd, J=8, 17 Hz, 1H), 2.85 (dd, J=6, 17 Hz, 1H), 2.72 (s, 3H), 1.92–1.48 (m, 8H). IR (KBr, cm$^{-1}$) 3420, 2940, 1755, 1660, 1600, 1510, 1430, 1440, 1320, 1255, 1230, 1150.

MS m/e (relative intensity) 475/473 (8/7, M+), 407/405 (7/5), 289 (30), 221 (100), 186/184 (17/21), 150 (49).

Analysis for: $C_{22}H_{24}BrN_3O_4$: Calculated: C, 55.71; H, 5.10; N, 8.86. Found: C, 55.34; H, 5.05; N, 8.80.

EXAMPLE 29

5-[3-(cyclopentyloxy)-4-methoxyphenyl]-1-methyl-2-[3-(3-pyridinyl)propyl]-3-pyrazolidinone quarter dichloromethane To a solution of 5-[3-(cyclopentyloxy)-4-methoxyphenyl]-1-methyl-3-pyrazolidinone (1.10 gms, 3.79 mmol), NaH (0.15 gms, 60%, 3.75 mmol), and dimethylformamide (15 mls) is added a solution of 1-bromo-3-(3-pyridinyl)propane [see Mioque, M., and Gautier, J. A. (1961). C. R. Hebd. Seances Acad. Sci. 252, 2416.] (1.66 gms, 8.30 mmol) in dimethylformamide (5 mls). The reaction is immersed in an oil bath (65° C.). After 20 hours dimethylformamide is removed in vacuo, the residue is diluted in methylene chloride, washed with saturated aqueous $NaHCO_3$ and dried over $Na_2SO_4$. The product was concentrated and chromatographed ($SiO_2$:1) 1:1 ethyl acetate:hexane; 2) 2:1 ethyl acetate:hexane; 3) ethyl acetate; 4) 3% methanol:ethyl acetate) to yield 0.85 gms (52%) of an oil. $^1H$ NMR (DMSO-$d_6$, 400 MHz) $\delta 8.40$ (m, 2H), 7.55 (m, 1H), 7.25 (m, 1H), 6.95 (s, 1H), 6.85 (m, 1H), 5.75 (s, 0.5H) 4.70 (m, 1H), 4.00 (m, 1H), 3.70 (s, 3H), 3.60 (m, 1H), 3.10 (m, 1H), 2.55 (s, 3H), 2.45 (m, 4H), 1.75 (m, 4H), 1.65 (m, 4H), 1.50 (m, 2H). IR(KBr, cm$^{-1}$) 1685 (C=O).

MS, m/z 410 (M+).

Analysis for: $C_{24}H_{31}N_3O_3 \cdot 0.25CH_2Cl_2$: Calculated: C, 67.62; H, 7.37; N, 9.75. Found: C, 67.50; H, 7.24; N, 9.55.

EXAMPLE 30

2-[(E)-3-(5-bromo-3-pyridinyl)-2-propenyl]-5-[3-(cyclopentyloxy)-4-methoxyphenyl]-1-methyl-3-pyrazolidinone hemi(dichloromethane)

A. 3-(5-bromo-3-pyridinyl)prop-2-en-1-ol

A solution of diisobutylaluminum hydride (DIBAL-H, 8.02 mls, 1.54M in toluene) in ether (50 mls) is cooled to −78° C. under $N_2$. A solution of 3-(5-bromo-3-pyridinyl)-2-propenoic acid ethyl ester [see Nishikawa, Y., et al.(1989) J. Med. Chem. 32, 583–593] (1.54 gms, 6.00 mmol) in ether (50 mls) is added. After one hour the dry ice/acetone bath is removed and the mixture is diluted with methylene chloride, dried over $Na_2SO_4$, evaporated and chromatographed (1:1 ethyl acetate:hexane followed by 2:1 ethyl acetate:hexane) to yield 1.08 gms of an oil (84%). $^1H$ NMR (DMSO, 300 MHz) $\delta 8.60$ (s, 1H), 8.50 (s, 1H), 8.15 (s, 1H), 6.60 (m, 2H), 5.00 (s, 1), and 4.10 (d, J=3.8 Hz, 2H).

B. 3-(5-bromo-3-pyridinyl)-1-chloroprop-2-ene

A solution of 3-(5-bromo-3-pyridinyl)prop-2-en-1-ol (0.85 gms, 3.97 mmol) is diluted with methylene chloride (20 mls). Thionyl chloride (0.27 mls, 97%, 1eq) is added at room temperature. After one hour a second equivalent of thionyl chloride is added. The reaction is neutralized with saturated aqueous NaHCO$_3$ after an additional hour and extracted with methylene chloride. The organic layer is dried over Na$_2$SO$_4$ and evaporated to yield 0.70 gms of an oil (76%). $^1$H NMR (CDCl3, 300 MHz) δ8.90 (s, 1H), 8.70 (s, 1H), 8.40 (s, 1H), 6.70 (m, 2H), and 4.30 (d, J=3.8 Hz, 2H).

C.
2-[(E)-3-(5-bromo-3-pyridinyl)-2-propenyl]-5-[3-(cyclopentyloxy)-4-methoxyphenyl]-1-methyl-3-pyrazolidinone hemi(dichloromethane)

To a stirred solution of 5-[3-(cyclopentyloxy)-4-methoxyphenyl]-1-methyl-3-pyrazolidinone (1.12 gms, 3.86 mmol) in dimethylformamide (10 mls) and NaH (0.16 gms, 60%, 4.0 mmol) is added 3-(5-bromo-3-pyridinyl)-1-chloroprop-2-ene (0.85 gms, 3.66 mmol). Dimethylformamide is removed in vacuo. The residue is diluted with methylene chloride, washed with saturated aqueous NaHCO$_3$, dried over Na$_2$SO$_4$, concentrated, and chromatographed (SiO$_2$:1) hexane; 2) 1:1 ethyl acetate:hexane; 3) 2:1 ethyl acetate:hexane; 4) 4:1 ethyl acetate:hexane; 5) ethyl acetate; 6) 9:1 ethyl acetate:methanol) to yield 0.50 gms(28%) of an oil. $^1$H NMR (DMSO, 400 MHz) δ8.55 ppm (m, 2H), 8.10 (m, 1H), 6.95 (s, 1H), 6.85 (s, 1H), 6.55 (d, J=16.2 Hz, 1H), 6.45 (d of t, J=17.1 Hz, J'=5.5 Hz, 1H), 5.75 (s, 1H), 4.65 (m, 1H), 4.35 (m, 1H), 4.05 (m,1H), 3.95 (m,1H), 3.70 (s,3H), 3.10 (m,1H), 2.55 (s,3H), 2.45 (m,1H), 1.60 (m,6H), 1.45 (m,2H). IR(CHCl3, cm$^{-1}$) 1690 (C=O). MS, m/z 486 (M+).

Analysis for: C$_{24}$H$_{28}$N$_3$O$_3$.0.5 CH$_2$Cl$_2$: Calculated: C, 55.64; H, 5.52; N, 7.94. Found: C, 55.82; H, 5.78; N 7.94.

EXAMPLE 31
2-acetyl-5-[3-(cyclopentyloxy)-4-methoxyphenyl]-1-methyl-3-pyrazolidinone hydrochloride 5-[3-(Cyclopentyloxy)-4-methoxyphenyl]-1-methyl-3-pyrazolidinone (0.500 g) is dissolved in acetic anhydride (15 mL). The resulting solution is warmed to reflux for 2 hours, cooled to room temperature and concentrated in vacuo to afford an oil. This residue is dissolved in ether and treated with ethanolic HCl at room temperature. The resulting solid is stirred for 4 hours at room temperature, collected by suction and dried in vacuo to afford the title compound as a white powder (0.621 g; 98%) mp: 82°-85° C. $^1$H NMR (DMSO-d$_6$, 400 MHz) δ6.88 (m, 3H); 3.85 (s, 3H); 2.82 (s, 3H); 2.52 (s, 3H); 2.00 (m, 2H); 1.84 (m, 3H); 1.64 (m, 2H). IR (KBr, cm$^{-1}$) 1730.

MS (EI, m/e) 332 (M+).

Analysis for: C$_{18}$H$_{24}$N$_2$O$_4$.HCl: Calculated: C, 58.61; H, 6.83; N, 7.59. Found: C, 58.41; H, 6.85; N, 7.80.

EXAMPLE 32
5-[3-(cyclopentyloxy)-4-methoxyphenyl]-1-methyl-2-(3-pyridinylcarbonyl)-3-pyrazolidinone hemihydrate To a solution of nicotinic acid (0.60 gms, 4.87 mmol) in benzene (5 mls) and dimethylformamide (0.05 mls, 0.646 mmol) is added oxalyl chloride (0.46 mls, 5.27 mmol) at room temperature. After 20 hours, the crude mixture is evaporated to 0.7 gms material. The crude product is added to a solution of 5-[3-(cyclopentyloxy)-4-methoxy-phenyl]-1-methyl-3-pyrazolidinone (0.70 gms, 2.41 mmol), NaH (0.1 gms, 60%, 2.5 mmol), and dimethylformamide (5 mls). The reaction is immersed in an oil bath (65° C.) and stirred 20 hours. Dimethylformamide is removed in vacuo. The residue is diluted with methylene chloride, washed with saturated aqueous NaHCO$_3$ and dried over Na$_2$SO$_4$. The product is concentrated, chromatographed (ethyl acetate), and recrystallized from methylene chloride/hexane to yield 275 mg of a white solid (28%, mp 83°-84° C.). $^1$H NMR (DMSO-d$_6$, 400 MHz) δ8.70 (m,2H), 7.90 (m,1H), 7.65 (m,1H), 7.05 (s,1H), 6.95 (s,1H), 4.75 (m,1H), 4.40 (m,1H), 3.70 (s,3H), 3.45 (m,1H), 2.85 (m,1H), 2.75 (s,3H), 1.85 (m,2H), 1.70 (m,4H), 1.55 (m,2H).

IR(KBr, cm$^{-1}$) 1760, 1665 (C=O). MS, m/z 395 (M+).

Analysis for: C$_{22}$H$_{25}$N$_3$O$_4$.½ (H$_2$O): Calculated: C, 65.33; H, 6.48; N, 10.39. Found: C, 65.18; H, 6.08; N 10.26.

EXAMPLE 33
2-[(E)-3-(5-bromo-3-pyridinyl)-1-oxo-2-propenyl]-5-[3-(cyclopentyloxy)-4-methoxyphenyl]-1-methyl-3-pyrazolidinone A mixture of 1-(3-dimethylaminopropyl)-3-ethylcarbodiimide hydrochloride (1.20 mmol, 0.230 g), 1-hydroxybenzotriazole hydrate (1.20 mmol, 0.162 g) and 3-(5-bromo-3-pyridyl)propenoic acid (1.20 mmol, 0.274 g [see Nishikawa, et al, *J Med Chem*, 32, 583 (1989)] is suspended in dry methylene chloride (20 mL) at room temperature and stirred for 2 hours. To the suspension is added a solution of 5-[3(cyclopentyloxy)-4-methoxyphenyl]-1-methyl-3-pyrazolidinone (1.20 mmol, 0.340 g) in dry methylene chloride (10 mL) and the resulting mixture is stirred at room temperature overnight followed by reflux for 24 hours. The homogenous solution is cooled to room temperature and the volatiles are removed in vacuo. The residue is partitioned between ethyl acetate (50 mL) and 1N NaOH (50 mL), the aqueous phase extracted with ethyl acetate (50 mL) and the combined organics are washed with water (50 mL) and dried (Na$_2$SO$_4$). Concentration in vacuo affords a white foam, which is purified via flash chromatography (SiO$_2$: concentration gradient ranging from 5% ethyl acetate/methylene chloride to 15% ethyl acetate/methylene chloride) to give the title compound as a white solid which is triturated with ether and hexane and dried in vacuo at 50° C. to provide analytically-pure material (0.52 mmol, 0.260 g, 52%). H-NMR (DMSO-d$_6$, 400 MHz) δ8.82 (d, 1H, J=1.7 Hz); 8.66 (d, 1H J=1.7 Hz); 8.41 (t, 1H); 7.71 (d, 2H, J=2.4 Hz,); 6.98 (d, 1H, J=1.5 Hz); 6.89 (m, 2H); 4.70 (m, 1H); 4.47 (dd, 1H, J=0.6, 1.7 Hz); 3.70 (s, 3H); 3.65 (m, 1H); 2.84 (s, 3H); 2.77 (m, 1H); 1.80 (m, 2H); 1.62 (m, 4H); 1.49 (m, 2H). IR (KBr, cm$^{-1}$) 3460, 2940, 2860, 1748, 1660, 1623, 1515, 1445, 1435, 1425, 1326, 1260, 1235, 1208, 1150, 1130, 1015, 990, 962, 848, 680.

MS (EI, m/e (%)) 502 (100), 500 (94), 291 (36), 234 (28).

Analysis for: C$_{24}$H$_{26}$BrN$_3$O$_4$: Calculated: C, 57.61; H, 5.24; N, 8.40. Found: C, 57.39; H, 5.46; N, 8.31.

EXAMPLE 34
5-[3-(cyclopentyloxy)-4-methoxyphenyl]-1-(phenylmethyl)-3-pyrazolidinone Sodium hydride (0.41 g of a 60% dispersion in mineral oil, 10.3 mmol, 1.1 equiv) is added to a solution of 5-[3-(cyclopentyloxy)-4-methoxyphenyl]-3-pyrazolidinone (2.6 g, 9.4 mmol, 1.0 equiv) in anhydrous N,N-dimethylformamide (20 mL), and the reaction mixture is stirred at room temperature for 20 minutes. Benzyl bromide (1.1 mL, 9.3 mmol), 1.0 equiv) in N,N-dimethylformamide is added dropwise and the resulting mixture is stirred at 70° C. for 60 hours. The solvent is removed in vacuo and the residue is taken up in methylene chloride, washed once with water, and then dried ($Na_2SO_4$). After chromatography on silica gel with hexanes/ethyl acetate, 1.5 g of solid is triturated with hexanes and ethyl acetate to give 1.0 g (29%) of a white solid identified as 5-[3-(cyclopentyloxy)-4-methoxyphenyl]-1-(phenylmethyl)-3-pyrazolidinone: mp 108°-110° C. $^1$H NMR ($d^6$-DMSO, 400 MHz) $\delta$9.50 (s, 1H), 7.37-7.21 (m, 5H), 6.89-6.79 (m, 3H), 4.70 (m, 1H), 4.17 (dd, J=5, 8 Hz, 1H), 3.97 (AB quartet, J=13 Hz, 1H), 3.80 (AB quartet, J=13 Hz, 1H), 3.69 (s, 3H), 2.99 (dd, J=8, 16 Hz, 1H), 2.17 (dd, J=5, 16 Hz, 1H), 1.91-1.49 (m, 8H). IR (KBr, $cm^{-1}$) 3420, 3150, 3020, 2960, 2860, 1690, 1590, 1515, 1450, 1430, 1375, 1340, 1260, 1230.

MS, m/e (relative intensity) 366 (19, M$^+$), 207 (28), 175 (41), 150 (57), 135 (47), 91 (100).

Analysis for: $C_{22}H_{26}N_2O_3$: Calculated: C, 72.11; H, 7.15; N, 7.64. Found: C, 72.06; H, 6.96; N, 7.63.

EXAMPLE 35

5-[3-(cyclopentyloxy)-4-methoxyphenyl]-1-ethyl-3-pyrazolidinone

Following the general procedure of Example 34, reaction with bromoethane (0.7 mL, 9.4 mmol, 1.0 equiv) gives, after chromatography on silica gel with hexanes/ethyl acetate, 0.35 g of solid, which is recrystallized from hexanes and ethyl acetate to yield 0.25 g (8.6%) of a white solid identified as 5-[3-(cyclopentyloxy)-4-methoxyphenyl]-1-ethyl-3-pyrazolidinone: mp 144°-148° C. $^1$H NMR ($d^6$-DMSO, 400 MHz) $\delta$9.53 (s, 1H), 6.94 (m, 1H), 6.87 (m, 2H), 4.75 (m, 1H), 4.03 (t, J=8 Hz, 1H), 3.70 (s, 3H), 2.87 (dd, J=8, 16 Hz, 1H), 2.71 (dq, J=7, 12 Hz, 1H), 2.53 (dq, J=7, 12 Hz, 1H), 2.21 (dd, J=8, 16 Hz, 1H), 1.92-1.48 (m, 8H), 0.98 (t, J=7 Hz, 3H). IR (KBr, $cm^{-1}$) 3420, 3160, 2960, 1680, 1590, 1515, 1445, 1430, 1380, 1350, 1255, 1230.

MS, m/e (relative intensity) 304 (22, M$^+$), 236 (8), 177 (100), 150 (78), 135 (40).

Analysis for: $C_{17}H_{24}N_2O_3$: Calculated: C, 67.08; H, 7.95; N, 9.20. Found: C, 66.70; H, 7.59; N, 9.12.

EXAMPLE 36

The following assay is employed to assess the ability of the compound of the invention to inhibit PDE IV.

A solution containing PDE IV is prepared from canine tracheal muscle as follows:

The dog is euthanized with an overdose of beuthanasia while under anesthesia induced by a 33 mg/kg IV bolus of Nembutal. The trachealis muscle is removed, cleaned of connective tissue, and minced thoroughly. Three to four grams of tissue is then homogenized in Tris-HCl buffer (pH 7.8) using a Polytron. The homogenate is then centrifuged at 25,000$\times$g (4° C.) for 30 minutes. The supernatant is decanted and filtered through four layers of gauze, and applied to a 40 cm$\times$2 cm DEAE-Sepharose column that is equilibrated with Tris-HCl buffer (pH 7.8). The column is then washed with an additional 240 mL of buffer to remove unbound proteins. PDE is eluted using 450 mL of Tris-HCl buffer containing a linear gradient of 0.0-1.0M Na-acetate (80 mL/hr), and 7.5 mL fractions are collected. Each fraction is assayed for cAMP- and cGMP- metabolizing PDE activity. Fractions eluting at approximately 0.6M Na-acetate, and containing cAMP but not cGMP metabolic activity are pooled and used as a PDE stock solution for assaying PDE IV inhibitory activity.

PDE IV activity is assayed [as described in Thompson et al., *Advances in Cyclic Nucleotide Research*, 10, 69 (1979)] at 30° C. in a reaction mixture containing: 10 mM Tris-HCl (pH 7.8), 5 mM $MgCl_2$, 1 mM $\beta$-mercaptoethanol, 1 $\mu$M $^3$H-cAMP, 10 $\mu$M CI-930, PDE IV stock solution, and the desired concentration of test compound. CI-930 is included as an inhibitor of the cyclic GMP-sensitive, cyclic AMP-selective PDE (PDE III) that is also present in the PDE IV stock solution when prepared as described above. The ability of a test compound to inhibit PDE IV is determined by measuring the reduction in cAMP metabolism produced by the test compound and expressing it as a percentage of the reduction induced by 10 $\mu$M rolipram, a potent inhibitor of PDE IV [see Beavo, *Advances in Second Messenger and Phosphoprotein Research*, 22, 1 (1988)]. $IC_{50}$'s are calculated for each test compound as the concentration of test compound that inhibits PDE IV by 50%.

When tested in this assay, the compounds of the invention give the following results.

TABLE 1

| Compound of Example No. | $IC_{50}$ of PDE IV |
|---|---|
| 1 | $3.4 \times 10^{-7}$ |
| 2 | $6.8 \times 10^{-7}$ |
| 3 | $8.2 \times 10^{-7}$ |
| 4 | $4.4 \times 10^{-7}$ |
| 5 | 39% ($10^{-5}$) |
| 6 | 52% ($10^{-5}$) |
| 7 | 39% ($10^{-5}$) |
| 8 | $1.6 \times 10^{-7}$ |
| 9 | $4.6 \times 10^{-7}$ |
| 10 | $3.1 \times 10^{-7}$ |
| 11 | $3.8 \times 10^{-7}$ |
| 12 | $4.2 \times 10^{-7}$ |
| 13A | $1.2 \times 10^{-8}$ |
| 13B | $1.8 \times 10^{-8}$ |
| 14 | $2.6 \times 10^{-7}$ |
| 15 | $4.9 \times 10^{-8}$ |
| 16 | 48% ($10^{-5}$) |
| 17 | $3.6 \times 10^{-8}$ |
| 18 | $1.0 \times 10^{-7}$ |
| 19 | $1.2 \times 10^{-7}$ |
| 20 | $6.5 \times 10^{-8}$ |
| 21 | $5.3 \times 10^{-8}$ |
| 22 | $2.1 \times 10^{-7}$ |
| 23 | $3.2 \times 10^{-7}$ |
| 24 | $8.5 \times 10^{-8}$ |
| 25 | $1.5 \times 10^{-6}$ |
| 26 | $1.7 \times 10^{-7}$ |
| 27 | $9.4 \times 10^{-7}$ |
| 28 | $3.5 \times 10^{-7}$ |
| 29 | $1.6 \times 10^{-7}$ |
| 30 | $5.0 \times 10^{-8}$ |
| 31 | $9.8 \times 10^{-7}$ |
| 32 | $3.4 \times 10^{-7}$ |
| 33 | $8.1 \times 10^{-8}$ |
| 34 | $5.8 \times 10^{-8}$ |
| 35 | $4.1 \times 10^{-6}$ |

The compounds tested in this assay exhibit significant activity in inhibiting PDE IV.

What is claimed is:

1. A compound having the formula

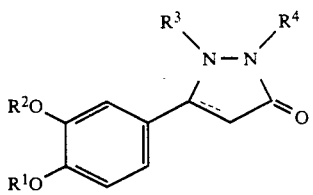

wherein
R¹ is hydrogen or lower alkyl;
R² is C₃₋₇ alkyl or C₃₋₇ cycloalkyl;
R³ is hydrogen, lower alkyl, carboxyloweralkyl, lower alkoxycarbonyl, lower alkoxycarbonyl loweralkyl, C₆₋₁₀ aryl or C₁₂₋₁₆ aralkyl;
R⁴ is

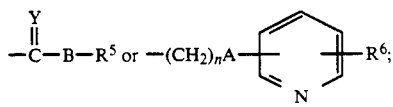

B is a bond, NH or O;
Y is O or S;
A is a bond or —C≡C—;
n is 0-5;
R⁵ is

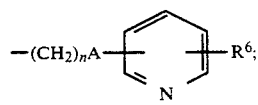

R⁶ is hydrogen or halo;
the dotted line represents an optional double bond; or a pharmacologically acceptable salt thereof.

2. A compound as claimed in claim 1 wherein

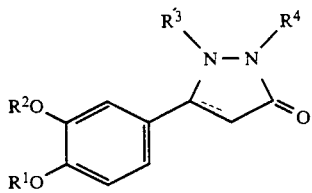

wherein
R¹ is C₁₋₃ alkyl;
R² is C₄₋₆ alkyl or C₅₋₆ cycloalkyl;
R³ is C₁₋₃ alkyl or C₁₂₋₁₆ aralkyl;
R⁴ is

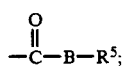

R⁵ is

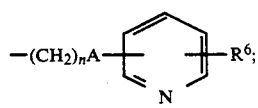

A is a bond or —C≡C—;
n is 0-2; and
R⁶ is hydrogen or halo.

3. A compound as claimed in claim 1 wherein

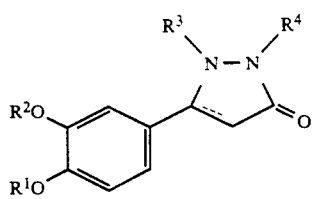

wherein
R¹ is lower alkyl;
R² is n-butyl or cyclopentyl;
R³ is methyl;
R⁴ is

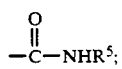

R⁵ is

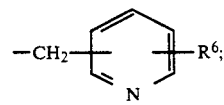

R⁶ is hydrogen or halo.

4. The compound of claim 1, having the name 3-[3-(cyclopentyloxy)-4-methoxyphenyl]-2,5-dihydro-2-methyl-5-oxo-N-(2-pyridinylmethyl)-1H-pyrazole-1-carboxamide.

5. The compound of claim 1, having the name 3-[3-(cyclopentyloxy)-4-methoxyphenyl]-2-methyl-5-oxo-N-(3-pyridinylmethyl)-1-pyrazolidine carboxamide.

6. The compound of claim 1, having the name 5-[3-(cyclopentyloxy)-4-methoxyphenyl]-1-methyl-2-(3-pyridinylmethyl)-3-pyrazolidinone hydrochloride dihydrate.

7. The compound of claim 1, having the name 2-[(5-bromo-3-pyridinyl)methyl]-5-[3-(cyclopentyloxy)-4-methoxyphenyl]-1-methyl-3-pyrazolidinone hydrochloride.

8. The compound of claim 1, having the name 5-[3-(cyclopentyloxy)-4-methoxyphenyl]-1-methyl-2-(5-bromo-3-pyridinylcarbonyl)-3-pyrazolidinone.

9. The compound of claim 1, having the name 5-[3-(cyclopentyloxy)-4-methoxyphenyl]-1-methyl-2-[3-(3-pyridinyl)propyl]-3-pyrazolidinone quarter dichloromethane.

10. The compound of claim 1, having the name 2-[(E)-3-(5-bromo-3-pyridinyl)-2-propenyl]-5-[3-(cyclopentyloxy)-4-methoxyphenyl]-1-methyl-3-pyrazolidinone hemi(dichloromethane).

11. The compound of claim 1, having the name 5-[3-(cyclopentyloxy)-4-methoxyphenyl]-1-methyl-2-(3-pyridinylcarbonyl)-3-pyrazolidinone hemihydrate.

12. The compound of claim 1, having the name 2-[(E)-3-(5-bromo-3-pyridinyl)-1-oxo-2-propenyl]-5-[3-(cyclo-pentyloxy)-4-methoxyphenyl]-1-methyl-3-pyrazolidinone.

* * * * *